(12) United States Patent
Jin et al.

(10) Patent No.: US 8,486,676 B2
(45) Date of Patent: Jul. 16, 2013

(54) CARRIERS FOR ENZYME OR CELL IMMOBILIZATION AND IMMOBILIZATION METHOD USING THE CARRIERS

(75) Inventors: Caike Jin, Hong Kong (CN); Jun Wang, Hong Kong (CN)

(73) Assignee: Bioright Worldwide Company Limited, Tortola (VG)

( * ) Notice: Subject to any disclaimer, the term of this patent is extended or adjusted under 35 U.S.C. 154(b) by 1205 days.

(21) Appl. No.: 12/097,671

(22) PCT Filed: Sep. 25, 2006

(86) PCT No.: PCT/CN2006/002512
§ 371 (c)(1),
(2), (4) Date: Oct. 8, 2008

(87) PCT Pub. No.: WO2007/068173
PCT Pub. Date: Jun. 21, 2007

(65) Prior Publication Data
US 2010/0028971 A1 Feb. 4, 2010

(30) Foreign Application Priority Data
Dec. 16, 2005 (CN) .......................... 2005 1 0132133

(51) Int. Cl.
*C12N 11/00* (2006.01)
*C12N 11/08* (2006.01)
*C12N 9/00* (2006.01)
*C12Q 1/00* (2006.01)

(52) U.S. Cl.
USPC ............... 435/174; 435/4; 435/180; 435/183

(58) Field of Classification Search
None
See application file for complete search history.

(56) References Cited

U.S. PATENT DOCUMENTS

| | | | |
|---|---|---|---|
| 3,809,605 A * | 5/1974 | Schmitt et al. | 435/179 |
| 4,355,105 A | 10/1982 | Lantero, Jr. | |
| 5,279,948 A * | 1/1994 | Pedersen et al. | 435/94 |
| 5,935,844 A | 8/1999 | Matsumura et al. | |
| 6,406,876 B1 * | 6/2002 | Gordon et al. | 435/20 |
| 6,881,837 B2 | 4/2005 | Deshpande et al. | |

FOREIGN PATENT DOCUMENTS

| | | |
|---|---|---|
| CN | 1216581 A | 5/1999 |
| CN | 1680558 A | 10/2005 |
| CN | 1702172 A | 11/2005 |
| CZ | 289772 | 4/2002 |
| JP | 5051482 | 5/1975 |
| JP | 51125790 | 11/1976 |

(Continued)

OTHER PUBLICATIONS

Matsuda et al., "Nucleotide Sequences of the Genes for Two Distinct Cephalosporin Acylases from a *Pseudomonas* Strain", Journal of Bacteriology, Dec. 1987, pp. 5821-5826, vol. 169, No. 12.

(Continued)

*Primary Examiner* — Yong Pak
(74) *Attorney, Agent, or Firm* — The Webb Law Firm

(57) ABSTRACT

The invention discloses a carrier made from an organic foam having open pores for enzymes or cells immobilization and the methods for preparing immobilized enzymes or cells. The invention uses flocculation and crosslinking technology to immobilize enzyme protein or cells on the organic foam material having open pores. The resultant immobilized products have larger specific surface area, higher specific activity and can be made into various shapes.

10 Claims, 1 Drawing Sheet

FOREIGN PATENT DOCUMENTS

| | | | |
|---|---|---|---|
| JP | 63202382 | A | 8/1988 |
| JP | 319687 | A | 1/1991 |
| JP | 3019687 | A | 1/1991 |
| JP | 638730 | A | 2/1994 |
| JP | 8256773 | A | 10/1996 |
| JP | 2001302840 | A | 10/2001 |
| JP | 2001347286 | A | 12/2001 |
| JP | 2003116762 | A | 4/2003 |
| JP | 2004129572 | A | 4/2004 |
| WO | 9117830 | A1 | 11/1991 |

OTHER PUBLICATIONS

Binder et al., "Biochemical Characterization of a Glutaryl-7-Aminocephalosporanic Acid Acylase from *Pseudomonas* Strain BL072", Applied and Environmental Microbiology, Jun. 1994, pp. 1805-1809, vol. 60, No. 6.

Shibuya et al., "Isolation and Properties of 7β-(4-Carboxybutanamido)cephalosporanic Acid Acylase-producing Bacteria", Agric. Biol. Chem., 1981, pp. 1561-1567, vol. 45, No. 7.

Markham et al., "S-Adenosylmethionine Synthetase from *Escherichia coli*", The Journal of Biological Chemistry, Oct. 10, 1980, pp. 9082-9092, vol. 255, No. 19.

Kikuchi et al., "Novel family shuffling methods for the in vitro evolution of enzymes", Gene, 1999, pp. 159-167, vol. 236.

Alonso et al., "D-Amino-acid oxidase gene from *Rhodotorula gracilis* (*Rhodosporidium toruloides*) ATCC 26217", Microbiology, 1998, pp. 1095-1101, vol. 144.

Isogai et al., "Structure and Expression of cDNA for D-Amino Acid Oxidase Active against Cephalosporin C from *Fusarium solani*", J. Biochem., 1990, pp. 1063-1069, vol. 108.

\* cited by examiner

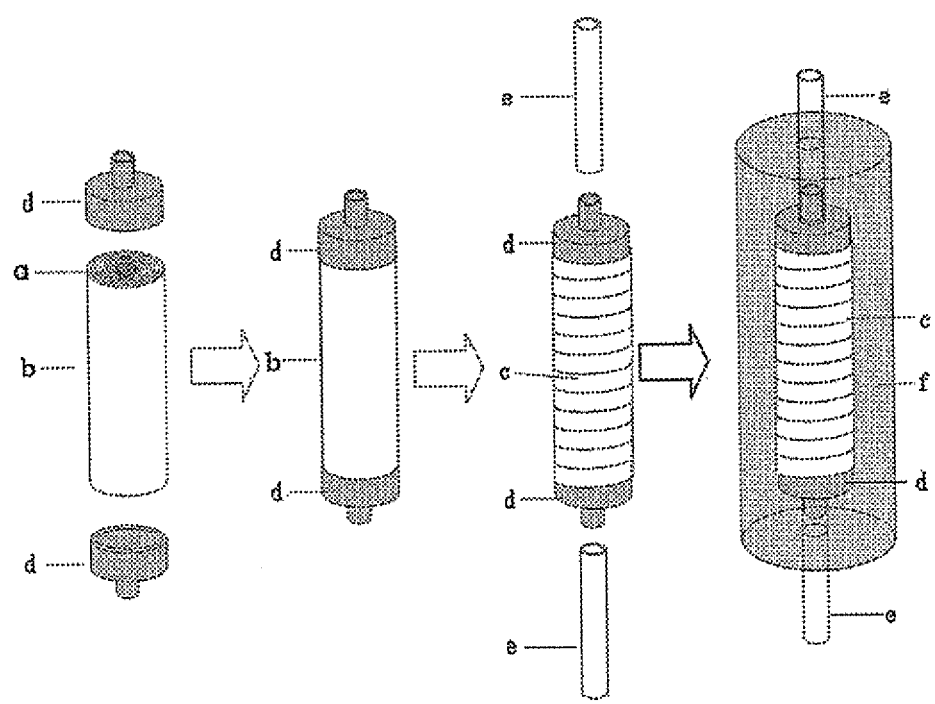

CARRIERS FOR ENZYME OR CELL IMMOBILIZATION AND IMMOBILIZATION METHOD USING THE CARRIERS

The Sequence Listing associated with this application is filed in electronic format via EFS-Web and is hereby incorporated by reference into the specification in its entirety. The name of the text file containing the Sequence Listing is 5449_081956_ST25.txt. The size of the text file is 56,893 bytes, and the text file was created on Feb. 14, 2012.

FIELD OF INVENTION

The invention relates to enzyme/cell immobilization technology, especially to the enzyme/cell immobilization technology using synthetic organic materials as carrier.

BACKGROUND OF THE INVENTION

With the advance of biotechnology, enzymes or enzyme-producing cells are often used for industry and other fields in immobilized form, for it is easy to separate and recover them from products for repeated usage, and they are more stable than free enzymes. There are many immobilization methods such as physical absorption, affinity linkage, covalent crosslinking, flocculation and encapsulation.

The level of the immobilization technology is usually assessed by the specific activity (the activity of unit weight of immobilized enzyme/immobilized cell). The specific activity is related to the immobilization method and to the surface area (specific surface area) of the unit weight of immobilized enzymes/cells. Generally, the larger the specific surface area is, the higher the specific activity is. Many immobilization methods therefore rely on the increase of the specific surface area of the enzyme particle. At present, the common methods for increasing the specific surface area include using porous and small sized carrier, and applying small particulate carriers having prefabricated capillary pores to adsorb or hold cells and enzymes.

However, the present technology is greatly restricted in increasing the specific surface area of immobilized enzymes/cells. The existing organic or inorganic carriers are mostly made from hard materials with the pores generally present on the surface of the carriers, for the carriers will easily be cracked if there are too many internal pores. Consequently, the scientists of the field are searching for immobilized carriers with large specific surface area and less prone to break.

SUMMARY OF THE INVENTION

To address the shortcomings of the existing carriers, which include (1) limited specific surface area; (2) only applicable to one or a few enzymes for immobilization and not applicable for cell immobilization and (3) usually expensive, the present invention aims to find an immobilization carrier that has large specific surface area, is less fragile, and can be applicable in immobilization of both enzymes and cells. Another technical issue of the present invention is to immobilize effectively enzymes or cells that express enzymes.

The invention utilizes organic foam materials containing open pores to increase the specific activity of immobilized enzymes/immobilized cells. The carrier has open pores inside the carrier, that is, the pore is not closed and there are at least two inter-connected pores. Using the described carrier, the immobilized products formed possess lattice-like 3D structure containing pores, and the reaction solution can flow through the internal of the immobilized enzymes/cells. It does not just increase the specific surface area significantly, but also minimizes the variation of the reaction rate between the surface and internal of the traditional granular immobilized products. Moreover, the immobilized enzymes/immobilized cells described in this invention, different from the existing products of granular or sheet shape, can be prepared in various sizes and different shapes such as granules, blocks, sheets or other shapes without significantly affecting its specific surface area.

The carrier in this invention is made from organic porous foam with open pore and water-absorptive property. The open pore of the carrier facilitates the entry of the enzymes into the internal of the carrier during immobilization, the interactions of substrate and enzyme during the reaction and the mass transfer of products after the reaction. The water-absorptive characteristic of the carrier enhances even distribution, proper adhesion and fixation of enzyme protein or cell and other hydrophilic components on the porous surface of the carrier. The stronger the absorptive property of the porous material is, the faster is the water natural wetting rate. The inventors of this invention have found that there is correlation between the suitability of the immobilization carrier and the rate of natural wetting of the porous material in water. A material is suitable as the immobilization carrier if the wetting rate is higher than 0.2 mm/second, preferably higher than 0.4 mm/second; while those with the rate lower than 0.2 mm/second is not suitable. The natural rate of wetting of many common synthetic materials (e.g polyurethane foam) in water is low. The materials selected for carrier in this invention include PVA foam, pulp foam and melamine foam.

This invention also provides a method of preparation of immobilized enzymes or immobilized cells, which includes the following steps:
  (i) Using porous organic foam with open pores as immobilization carrier; and
  (ii) Using flocculation and crosslinking to immobilize the enzymes or cells on the carrier.

The invention has a number of advantages over the present technology. Firstly, the porous organic foam with open pores as the carrier for immobilized enzymes or cells increases the specific surface area substantially and enhances the specific activity of the immobilized enzymes/immobilized cells significantly. Secondly, the methods in the invention can be broadly used for applied enzymology, and theoretically, the method is almost applicable for immobilization of enzymes and cells of various types. Thirdly, the carrier uses inert materials, which are cheap, and therefore reduces the production cost. Fourthly, the carrier is not made of rigid materials and is less prone to break even under vigorous stirring. Fifthly, the products in this invention can be tailor-made to various shapes and size without changing the specific surface area, which is especially useful for large scale industrial production.

BRIEF DESCRIPTION OF THE DRAWING

FIG. 1 shows the preparation of packed bed immobilized column loaded with reel-shaped carrier having immobilized cells thereon, a: inner core, b: reel-shaped carrier with cells immobilized therein, c: rubber band, d: interface device, e: silicone tube, f: polyurethane insulation materials.

DETAILED DESCRIPTION OF THE INVENTION

As mentioned above, the carrier in this invention is made of porous organic foam with open pores, having a water natural wetting rate of at least 0.2 mm/second. The water wetting rate is determined as follows: the dried organic porous material is cut into cubes of 5 cm in length, and when the material is placed gently on the surface of distilled water of 20 cm in depth, timing is started at once. The testing is terminated either the material is completely wetted or 10 minutes after the timing was started. Under this condition, the "water natural wetting rate" of the material is defined as the ratio of the vertical height (in mm) of the wetted portion (includes the portion immersed in water) of the organic porous material to the time taken (in second).

The inventors consider those porous organic foam materials that carry hydrophilic groups such as hydroxyl, amino, or cyano groups on the backbone or branch chains of the polymers are likely suitable materials for the carrier. Among the porous organic materials with open pores commercially available from the market polyvinyl alcohol foam, pulp foam and melamine foam are suitable materials for the carrier. The carriers made from these materials can be made into different shapes such as granules, straps, sheets, columns or blocks.

The invention also provides a method of immobilization of enzymes or cells on the carrier invented. Before the immobilization of enzymes and cells, the carrier is cut into sheets or granules; the enzyme solution or cell suspension is adjusted to appropriate concentration using water or buffer. An embodiment of the immobilization method of the invention is shown as follows: a) the enzyme solution or cell suspension is added into the carrier, pressed by hand to distribute the liquid evenly on the carrier and remove those liquid that is not adsorbed; b) appropriate amount solution of protein flocculation agent is added into the carrier that has adsorbed enzyme solution, pressed by hand several times to allow enzymes or cells to flocculate and deposit on the pore walls of the carrier; and pressed by hand again to remove unadsorbed liquid; c) appropriate amount of crosslinking agent solution is added into the carrier to cross-link and immobilize the flocculated proteins or cells, then the carrier is pressed by hand to remove crosslinking agent solution; and d) the steps (a) to (c) are repeated if necessary to increase the amount of the enzymes or cells loaded on the carrier. Finally, the carrier is washed with water several times and dried. Another alternative embodiment of the immobilization method of the invention is shown as follows: a') an amount of multi-aldehyde compounds used as crosslinking agent is added to an enzyme or cell containing solution to be immobilized to generate solutions of aldehyde-modified enzymes or cells; b') the above described aldehyde-modified enzyme or cell solution is added into the cut carrier, which is pressed by hand to distribute the solution evenly; c') an amount of protein flocculant is added into the carrier, which is pressed by hand several times to make the components mixed and then pressed by hand again to remove the liquid on the carrier; d') steps (a') to (c') are repeated several times if necessary to increase the amount of enzymes or cells loaded on the carrier. Finally, the carrier is washed with water several times and dried.

During the immobilization of enzymes or cells, the carrier can be pressed by hand or by special device or machines. The pH of the buffers used should consider the optimal activity of the enzyme and make sure that the surface charges of the enzyme and the flocculant are in the opposite. Generally, the concentration of the enzyme proteins used is 0.3%-30% (W/V), concentration of the cells is 1-50% (V/V), concentration of the flocculant is 0.01%-30% (VN) and that of the crosslinking agent is 0.01%-30% (V/V). The flocculant used is usually of large cation molecules such as chitosan, polyethyleneimine (PEI), carboxymethyl polyethyleneimine (CMPEI), etc. The crosslinking agent is generally of multi-aldehyde compounds (e.g glutaraldehyde, dialdehyde starch, glucan di-aldehyde). The flocculant or crosslinking agent can be used alone or mixed together to use. Non-enzyme proteins such as serum protein, ovalbumin, whey protein or cheese protein can be added into the enzyme solution to reduce amount of the enzyme used and improve the activity of the recovered enzymes. In addition, to meet the requirements of different products, the additional steps of the immobilization or other components can be added to enhance product's performance in terms of activity, stability, permeability, specificity or appearance characteristic, etc.

The granular form of the immobilized enzymes or cells prepared in this invention can be used in stirred tank reactor or packed-bed reactor. The sheet shaped products can be rolled into cylindrical reel structure and form the reaction column directly. Such reel structured products can be used as blocks, and packed and disposed inside the bioreactor, or used alone or in combination with each other to form reaction columns with adjustable diameter or length for industrial production.

The tension generated from the rolling operation and the continuous pressure applied to the porous material against the inner core during the rolling of sheet shaped products of the invention results in modest compression of the porous material. This rolling process is therefore a process of formation of the reel structured product as well as a process of compression of the porous material. The degree of the tightness of the reel structure can be adjusted by adjusting the pressure applied to the porous material. The diameter of the reel structure can be controlled by the numbers of the rolling and the thickness of the carrier material. The height of the reel-cylinder can be controlled by changing the width of the carrier or by cutting the reel structure into the required height directly.

The columnar surface of the described cylindrical reel column can be fixed and sealed by using a suitable packing material to prevent the loosening of the windings. The packing should be made of a water-adsorbing and swelling material such as dried PVA foam and pulp foam, if the immobilized enzyme itself does not possess such property, to reduce the gap that may exist between the column surface and the inner wall of the column holder after filling the reaction tank with water. Such gap can also be tamped with granular material. The cylindrical reel column should be wrapped with waterproof and insulation material such as polyurethane foam to reduce energy consumption when it is used as reactor column alone or together with other columns without column holder. On the other hand, if the cylindrical reel column shrinks and the volume reduces during the reaction, the packing material, should possess property of continuous shrinkage, for example rubber or material contained rubber to avoid the development of the gap.

When the cylindrical reel column is used alone or together with other columns, the both ends of the columns should have a device that connects column and tubes to allow the efficient inflow and outflow of the reaction solution and have a function of filtration. When used in tandem, the cylindrical reel columns should be sealed with rubber band to prevent leakage between the columns.

DESCRIPTION OF THE PREFERRED EMBODIMENT

The examples presented below are for illustration of the invention only and are not intended to be regarded as the limitation of the invention. In the following examples, conventional practice or manufacturers' suggestion/protocol was followed in cases where the conditions were not specified.

Example 1

The Water Natural Wetting Rate of the Organic Porous Material

The dried organic porous material was cut into cubes of 5 cm in length, and when the material was placed gently on the surface of distilled water of 20 cm in depth, the timing was started at once. The test was terminated 10 minutes after the timing was started or when the material was completely wetted. Under this condition, the water natural wetting rate of the material was defined as the ratio of the height (in mm) vertical to the water surface of the wetted portion (including the portion immersed in water) of the organic porous material to the time (in second) taken to wet the portion of the material. A number of organic porous materials had been tested and the results were shown in Table 1.

TABLE 1

| Product designation | model | Source | Specific Density ($g/cm^3$) | Wetting Rate (mm/second) | Whether being Able to Immobilize Cells Evenly or not |
|---|---|---|---|---|---|
| Polyester Foam | ST33 | Shenzhen Lian Da Industry Co Ltd | 0.0501 | <0.01 | No |
| Polyurethane Foam | DL68 | Shenzhen Lian Da Industry Co Ltd | 0.0314 | <0.01 | No |
| Polyurethane Foam | L338 | Shenzhen Lian Da Industry Co Ltd | 0.0213 | <0.01 | No |
| Polyurethane Foam | A230 | Shenzhen Lian Da Industry Co Ltd | 0.0186 | <0.01 | No |
| Polyurethane Foam | — | US Stepan Company | 0.0250 | <0.01 | No |
| Polyurethane Foam | — | Singapore Yi Zhan Gong Ye Co Ltd | 0.0365 | <0.01 | No |
| Polyester Fiber | — | Shenzhen Lian Da Industry Co Ltd | 0.0351 | 0.044 | No |
| PVA Foam | — | Shenzhen Junhong Co Ltd | 0.1191 | 0.483 | Yes |
| Pulp Foam | — | 3M Hong Kong Ltd | 0.0830 | 1.75 | Yes |
| Melamine Foam | — | Zhuhai Tin Hong Special Sponge Factory | 0.0080 | 12.50 | Yes |

Example 2

Immobilization of E. coli Cells Containing Expressed Glucose Isomerase on Granular Carriers (I)

Based on the sequence of pGEMT-Easy (Promega), the following primers RBS-NdeI and RBS-AlwNI for PCR were designed:

```
Forward primer RBS-NdeI:
                                      (SEQ ID NO: 15)
5'-CATATGTATATCTCCTTCTTGTGTGAAATTG-3'

Reverse primer RBS-AlwNI:
                                      (SEQ ID NO: 16)
5'-CAGTGGCTGCTGCCAGTGGCGATAAGTC-3'
``` a DNA fragment of 755 bp was obtained by PCR amplification using pGEMT-Easy (Promega) as template, and the RBS-NdeI and RBS-AlwNI as primers. The PCR amplification condition was: 50 ng pGEMT-Easy (Promega), 0.4 μM RBS-NdeI, 0.4 μM RBS-AlwNI, 50 μM dATP, 50 μM dTTP, 50 μM dCTP, 50 μM dGTP, 20 mM Tris-HCl (pH 8.8), 10 mM KCl, 10 mM $(NH_4)_2SO_4$, 2 mM $MgSO_4$, 0.1% Triton X-100, 2.5 U Pfu DNA Polymerase (Promega), and the volume was adjusted to 50 μl with sterile distilled water. PCR amplification program for the reaction was: 94° C., 5 minutes; then 35 cycles of 94° C., 1 minute; 50° C., 1 minute; 72° C., 4 minutes; and 72° C., 10 minutes. The PCR products (755 bp) contained NdeI enzyme cutting site and a ribosome binding site at the 5' end, and an AlwNI enzyme cutting site at the 3' end. The fragment was separated by 0.8% agarose gel electrophoresis, purified, digested with NdeI and AlwI, and ligated with NdeI and AlwNI digested pRSETA (Invitrogen) to generate pRSET-lac. pRSET-lac and pRSET-kan (China Patent Application Publication No: CN1680558A) were digested with AlwI and EcoRI, and the obtained fragments were separated by 0.8% agarose electrophoresis, purified, and ligated to generate pRSET-lac-kan.

According to the method of preparation of glucose isomerase mutant as described in the Chinese Patent Application Publication No. CN1702172, the gene of MGI4-35 of glucose isomerase mutant containing seven mutations of F87L, W139F, R182A, F187S, V217G, D260A and T299Q was obtained by PCR amplification using primer pairs T1 and 87LR, 87LF and 217GR, 217GF and 260AR, 260AF and T2 (Table 2) and pGEMT-MGI-4 as the template. MGI4-35 was digested with NdeI and EcoRI, and ligated with NdeI and EcoRI digested pRSET-lac-kan to generate plasmid pRSET-lac-MGI4-35-kan. The complete sequence of the plasmid pRSET-lac-MGI4-35-kan was shown in Sequence 1 as in the Sequence Listing.

TABLE 2

Primer Pair

T1: 5'AGCCTAGGTTAATTAACTTTAAGAAGGAGATATACATATGAATAAATATTTTGAGA 3' (SEQ ID NO: 17)

87LR: 5'AAAAACTCCAGTGCTGCTTCTACCCTTGCTTTC 3'(SEQ ID NO: 18)

87LF: 5'GAAGCAGCACTGGAGTTTTTTGATAAGATAA 3'(SEQ ID NO: 19)

217GR: 5'GCATAGTCGCCAGCCATGTGCAAAAATCTT 3'(SEQ ID NO: 20)

TABLE 2-continued

Primer Pair

```
217GF:  5'ACATGGCTGGCGACTATGCAAAGGAAATCG 3'(SEQ ID NO: 21)

260AR:  5'AAATATTTCGCAAGGTCGTATTTTCTCAAG 3'(SEQ ID NO: 22)

260AF:  5'ACGACCTTGCGAAATATTTCAAAGTAAATA 3'(SEQ ID NO: 23)

T2:     5'ATAAGCTCAGCGGCGCGCCTTATTCTGCAAACAAATAC 3'(SEQ ID NO: 24)
```

The plasmid pRSET-lac-MGI4-35-kan was transformed into *E. coli* BL21 (DE3) pLysS. The *E. coli* transformant containing MGI4-35 was inoculated into 70 L LB liquid medium (containing 50 mg/L kanamycin) in 1% inoculums and incubated at 37° C. for 36 hours. 670 g of wet cell pellets was collected after centrifugation and resuspended in equal weight of distilled water.

6 grams of dried PVA foam (Hao Bang Shou Ri Yong Pin Co Ltd, Ninghai County Zhejiang Province) were cut into 15 mm³ cubes and put inside a nylon mesh bag, which was then placed in a plastic bag. 40 ml of the cell suspension of *E. coli* was added into the foam cubes, pressed by hand repeatedly for at least 3 minutes to make the components mixed so as to ensure the even distribution of the cell suspension on the foam. 40 ml of 0.5% (w/v) pH 7.0 PE (Sigma Chemicals, St. Louis, USA) was added into the foams, pressed by hand repeatedly for at least 3 minutes to make the components mixed. 40 ml of 0.5% (v/v) glutaraldehyde solution (Xilong Chemical Industry Factory Co. Ltd, Shantou, Guangdong) was added into the foams, pressed by hand repeatedly for at least 5 minutes to make the components mixed. The nylon mesh bag was taken out from the plastic bag and pressed by hand to remove liquid. It was then pressed by hand again and washed with water three times to remove the unadsorbed liquid. It was dried under flow air for 5-10 hours to get 11 g granules of immobilized *E. coli* cells containing expressed glucose isomerase.

The specific activity of the immobilized cells prepared in the example was measured according to the method of enzyme activity assay as described in the references (Dische et al., 1951, J. Biol. Chem, 192:583-587; Nakamura, 1968, Agr. Biol. Chem. 32.701-706). Specifically, 1 ml of 36% (w/v) glucose solution (containing 0.25 mM $CoCl_2$, 5 mM $MgCl_2$, 20 mM phosphate solution, pH6.5) was added to 0.5-2 mg of immobilized cells particles obtained as described above, and the obtained solution was shaked at 75° C. to react for 10 minutes and placed on ice bath to stop the reaction. 1 unit of glucose isomerase activity is defined as the amount of enzyme required to convert 1 µmole of glucose into fructose in 1 minute under the above condition. The specific activity of the immobilized cells prepared as described in Example 2 was 2,540 U/g.

Example 3

Immobilization of *E. coli* Cells Containing Expressed Glucose Isomerase on Granular Carriers (II)

40 ml cell suspension prepared as described in Example 2 was mixed with 6 ml of 0.25 mM $CoCl_2$ to uniformity. Pulp foam (3M Hong Kong Ltd) was washed thoroughly to remove any surfactants, cut into particles of roughly 15 mm³ in size and dried up. 4 grams of dried foam cubes were placed into a nylon mesh bag, which was then placed inside a plastic bag, and added with the 46 ml cell suspension containing $CoCl_2$. The mixture was pressed by hand for at least 3 minutes to make the components mixed so as to ensure even distribution of the liquid in the foams, into which 10 ml of 2.5% PEI solution (pH 7.0) was added, pressed by hand again repeatedly for at least 3 minutes to make the components mixed; 10 ml of 2.5% glutaraldehyde solution was added and the mixture was pressed by hand repeatedly for at least 5 minutes to make the components mixed. The nylon mesh bag was then taken out from the plastic bag, pressed by hand again to remove liquid, then pressed by hand and washed with water 3 times to remove the unadsorbed liquid and dried under flow air for 5-10 hours. 9 grams particles of immobilized *E. coli* cells containing expressed glucose isomerase were obtained.

The activity of glucose isomerase was measured as described in Example 2. The specific activity of the immobilized cells prepared in Example 3 was 4,442 U/g.

Example 4

Immobilization of *E. coli* Cells Containing Expressed Glucose Isomerase on Granular Carriers (III)

As described in Example 2, cell suspension was prepared. 2.67 g of dried melamine foam with open pores content>95% (Zhuhai Tin Hong Special Sponge Factory) were cut into 15 mm³ cubes and placed inside a nylon mesh bag, which was then placed inside a plastic bag. 80 ml of the cell suspension was added to the foam cubes, pressed by hand repeatedly for at least 3 minutes to make the components mixed so as to ensure even distribution of the cell suspension on the foams. 160 ml of 0.5% PEI solution (pH 7.0) was added into the foams, pressed by hand repeatedly for at least 3 minutes to make the components mixed, pressed by hand again to remove unadsorbed liquid. 160 ml of 0.5% glutaraldehyde solution was added into the foams, pressed by hand repeatedly for at least 3 minutes to make the components mixed. The nylon mesh bag was taken out from the plastic bag and pressed by hand to remove liquid. It was then pressed by hand again and washed with water three times to remove the unadsorbed liquid. It was dried under flow air for 5-10 hours to get 13 g granules of immobilized *E. coli* cells containing expressed glucose isomerase.

The activity of glucose isomerase was measured as described in Example 2. The specific activity of the immobilized cells prepared in Example 4 was 5,544 U/g Example 5

Immobilization of *E. coli* Cells Containing Expressed Glucose Isomerase on Granular Carriers (IV)

The cell suspension was prepared as described in Example 2. The cells were suspended in five volumes of distilled water.

10 grams of melamine foams were cut into cubes of 15 mm³, placed in a nylon mesh bag and immobilized as follows: a) the foam cubes were immersed in 1,000 ml of the cell suspension for at least 3 minutes, taken out and pressed by hand to remove the unadsorbed liquid; b) 100 ml of 0.1% PEI solution (pH 7.0) was added into the foams, which were pressed by hand for at least 3 minutes to make the components mixed, and then pressed by hand again to remove unadsorped liquid; c) 100 ml of 0.1% glutaraldehyde solution was added into the foams, which were pressed by hand to make the components mixed, and kept stand for 3 minutes, then pressed by hand again to remove unadsorbed liquid; d) the steps (a) to (c) were repeated five times, then pressed by hand and washed three times with water, pressed by hand again to remove unadsorbed liquid, and dried under flow air for 5-10 hours. 60 grams granules of immobilized E. coli cells containing expressed glucose isomerase were obtained.

The activity of glucose isomerase was measured as described in Example 2. The specific activity of the immobilized cells prepared in Example 5 was 6,150 U/g Example 6

Immobilization of E. coli Cells Containing Expressed Glutaryl-7-Aminocephalosporanic Acid Acylase on Granular Carriers Construction of pT7-kan-ACY: based on the DNA sequence of Pseudomonas SE83 glutaryl-7-aminocephalosporanic acid acylase (Matsuda, A. et al., 1987, J. Bacteriol. 169, 5821-5826), the following primers were designed:

```
Forward primer NdeI-ACY
                                  (SEQ ID NO: 25)
5'-CATATGAACGCTCCCGTCCCCGTCCC-3'

Backward primer BglII-ACY:
                                  (SEQ ID NO: 26)
5'-AGATCTTCAGATGGTGAAGCGGGCAC-3'
```

Using Pseudomonas SE83 as the template, and the primers NdeI-ACY and BglII-ACY, a DNA fragment of 1,676 bp was amplified. The amplification condition was: 50 ng Pseudomonas SE83 DNA, 0.4 µM NdeI-ACY, 0.4 µM BglII-ACY, 50 µM dATP, 50 µM dTTP, 50 µM dCTP, 50 µM dGTP, 20 mM Tris-HCl (pH 8.8), 10 mM KCl, 10 mM $(NH_4)_2SO_4$, 2 mM $MgSO_4$, 0.1% Triton X-100, 2.5 U Pfu DNA polymerase (Promega), and the volume was adjusted to 50 µl with sterile distilled water.

PCR amplification program for the reaction was: 95° C., 5 minutes; then 35 cycles of 94° C., 1 minute; 50° C., 1 minute; 72° C., 3 minutes; and 72° C., 10 minutes. The PCR products (1,676 bp) contained NdeI and BglII enzyme cutting sites at 5' and 3' ends respectively. The PCR fragment was separated by 0.8% agarose gel electrophoresis, purified, digested with NdeI and BglII and ligated with NdeI and BglII digested pRSET-kan to generate pT7-kan-ACY. The sequence was shown as Sequence 2 in the Sequence Listing. The competent cells of E. coli BL21(DE3)pLysS (Novagen) were transformed with pT7-kan-ACY to generate BL-T7K-ACY.

The cells of E. coli BL-T7K-ACY were incubated in 20 L LB medium containing kanamycin (50 mg/L) at 37° C. for 24 hours and 235 g of wet cell pellets was obtained after centrifugation. The pellet was then suspended in five times weight of distilled water.

10 grams of melamine foams were cut into cubes of 15 mm³, placed in a nylon bag and immobilized as follows: a) the foam cubes were immersed in 1,000 ml of the cell suspension for at least 3 minutes, taken out and pressed by hand to remove the unadsorbed liquid; b) 100 ml of 0.1% PEI solution (pH 7.0) was added into the foams, pressed by hand repeatedly for at least 3 minutes to make the component mixed, and then pressed by hand again to remove unadsorbed liquid; c) 100 ml of 0.1% glutaraldehyde solution was added into the foam, pressed by hand repeatedly to make the components mixed, and then kept to stand for 5 minutes, pressed by hand again to remove unadsorbed liquid; d) the steps (a) to (c) were repeated five times, then pressed by hand and washed with water, pressed by hand again to remove unadsorbed liquid and dried under flow air for 5-10 hours. 50 grams granules of immobilized E. coli cells containing expressed GL-7-ACA acylase were obtained.

The specific activity of immobilized E. coli cells containing expressed GL-7-ACA acylase was measured according to Binder, R. et al., (1994, Appl. Environ. Microbiol. 60, 1805-1809). Specifically, 18 g of the immobilized cells containing expressed GL-7-ACA acylase were resuspended in 600 ml of 75 mM glutaryl-7-aminocephalosporanic acid solution (containing 25 mM sodium phosphate, pH 8.0) (the preparation of glutaryl-7-aminocephalosporanic acid was performed according to Shibuya, Y et al., 1981, Agric. Biol. Chem. 45, 1561-1567) and allowed the obtained mixture to react at 37° C. with stirring (450 rpm). The pH 8.0 was maintained with 5N sodium hydroxide. 60 µl of sample was collected at time of 0, 10 and 20 minutes after the reaction started and the reaction was terminated by adding 30 µL 10% TCA to the sample until uniformity. The reaction mixture was centrifuged (10,000 g, 3 minutes) and 10 µL of the supernatant was mixed with 990 µL HPLC mobile phase (50 mM sodium phosphate, pH 7; 5% acetonitrile). The enzyme reaction was assessed with HPLC under the following condition: HPLC column: Diamonsil™ C18, 250 4.6 mm (Dikma Technologies, Beijing); column temperature: 30° C.; flow rate: 1 mL/minute; detection wavelength: 260 nm. 1 unit of GL-7-ACA acylase activity was defined as the amount of enzyme required to convert 1 µmole of glutaryl-7-aminocephalosporanic acid into 7-aminocephalosporanic acid in 1 minute under the above condition. The specific activity of the immobilized cells prepared in Example 6 was 140.8 U/g in the initial 10 minutes.

Example 7

Immobilization of E. coli Cells Containing Expressed Adenosylmethionine Synthetase on Granular Carriers Primer pair SAM-F and SAM-R was designed according to the GENBANK NC_000909. The sequence of SAM-F was:

```
The sequence of SAM-F was:

5'AGCCTAGGTTAATTAACTTTAAGAAGGAGATATACATATGAGAAACAT
                                       (SEQ ID NO: 27)
AATTGTAA 3';

The sequence of SAM-R was:
                                       (SEQ ID NO: 28)
5' ATAAGCTCAGCGGCGCGCCTTAGAATGTAGTTACTTTTCCTTCA 3'
```

Using Methanococcus jannaschii JAL-1 ATCC 43067 (ATCC, USA) as DNA template, and the primers SAM-F and SAM-R, the gene of S-adenosylmethionine synthetase was amplificated under the amplification condition as follows: 20 mM Tris-HCl (pH8.8), 10 mM KCl, 10 mM $(NH_4)_2SO_4$, 0.1% Triton X-100, 50 μA dATP, 50 μM dTTP, 50 μM dCTP, 50 μM dGTP, 400 nM SAM-F, 400 M SAM-R, 4.5 U Taq DNA polymerase (Promega, USA). The volume was adjusted to 50 μl with sterile distilled water. PCR amplification was programmed as follows: 95° C., 3 minutes; then 40 cycles of 95° C., 50 seconds; 50° C., 30 seconds; 72° C., 1 minute; and finally 72° C., 10 minutes. The amplified fragment (1.3 KB in length) was cloned into pRSET-lac-kan and the product was transformed into E. coli BL21(DE3)pLysS, which was then cultured on LB plate (containing 50 mg/L kanamycin) overnight. Single colony was isolated.

The cells of E. coli BL21(DE3)pLysS containing the expressed M. jannaschii S-adenosyl methionine synthetase were incubated in 1% inoculums in 50 L LB medium containing kanamycin (50 mg/L) at 37° C. for 40 hours and 480 g of wet cell pellet was obtained after the centrifugation. The pellet was then resuspended in five times weight of distilled water.

10 grams of melamine foams were cut into cubes of 15 mm³ and placed in a nylon bag. Then immobilization was performed as follows: a) the foam cubes were taken out after immersed in 1,000 ml cell suspension for at least 3 minutes, and pressed by hand to remove the unadsorbed solution; b) 100 ml of 0.1% PEI solution (pH 7.0) was added into the foams, which were pressed by hand repeatedly for at least 3 minutes to make the component mixed, and then pressed by hand again to remove unadsorbed solution; c) 100 ml of 0.1% glutaraldehyde solution was added into the foams, which were pressed by hand repeatedly to make the component mixed, kept stand for 5 minutes, and then by hand again to remove unadsorbed liquid; d) the steps (a) to (c) were repeated three times, and then the foams were pressed by hand and washed with water, treated with 70° C. water for 30 minutes, and pressed by hand again to remove unadsorbed liquid, and the foams were dried under flow air for 5-10 hours. 50 grams granules of immobilized E. coli cells containing expressed adenosyl methionine synthetase were obtained.

The activity of the enzyme was measured according to George D. Markham et al (1980, Journal of Biological Chemistry, 255, 9082-9092). Specifically, 15 mg of immobilized cells were added into 500 μl reaction buffer (2 mM ATP, 8 mM L-methionine, 20 mM MgCl₂, 100 mM KCl, 100 mM Tris-Cl pH8.3) and the reaction was allowed to process at 58° C. with shaking for 20 minutes. The reaction was terminated by adding 300 μl 10% TCA. The reaction mixture was then centrifuged to remove precipitates. The quantity of the SAM in supernatant was assayed by HPLC. The HPLC assay was performed as described in U.S. Pat. No. 6,881,837 (HPLC column: C18, 4.6 mm×250 mm, Beckman Coulter; USA; buffer: 0.02 M citric acid, 0.01 M sodium dihydrogen phosphate; mobile phase: a. 0.4% SDS containing buffer; b. acetonitrile; the ratio of a to b is 56:44; flow rate: 1.5 ml/minute; detection wavelength: 260 nm). The specific activity of the immobilized cells prepared in Example 7 was 0.6 U/g.

Example 8

Immobilization of D-Amino Acid Oxidase on Granular Carriers

The preparation of strain BL-HS-GHA (the cells of E. coli BL21 (DE3) pLysS containing recombinant D-amino acid oxidase GHA) was as follows:
The origin of BL-HS-GHA:
Based on the DNA sequence of Thermoanaerobacterium saccharolyticum glucose isomerase (GenBank L09699), the following PCR primers were designed:

The forward primer:
(SEQ ID NO: 29)
5'-AGCCTAGGTTAATTAACTTTAAGAAGGAGATATACATATGAATAAAT
ATTTTGAGA The reverse primer:
(SEQ ID NO: 30)
5'-ATAAGCTCAGCGGCGCGCCTTATTCTGCAAACAAATAC Using Thermoanaerobacterium saccharolyticum (ATCC, USA) as DNA template, and the forward and reverse primers, a DNA fragment of 1,376 bp was amplified. The PCR amplification condition was: 50 ng T. saccharolyticum DNA, 0.4 mM GI-NdeI, 0.4 μM GI-EcoRI, 50 μM dATP, 50 μM dTTP, 50 μM dCTP, 50 μM dGTP, 20 mM Tris-HCl (pH 8.8), 10 mM KCl, 10 mM (NH₄)₂SO₄, 2 mM MgSO₄, 0.1% Triton X-100, 2.5 U Platinum Taq High Fidelity DNA polymerase (Invitrogen), and the volume was adjusted to 50 μL wilt sterile distilled water. PCR amplification was programmed at: 95° C., 5 minutes; then 35 cycles of 94° C., 1 minute; 50° C., 1 minute; 72° C., 3 minutes; and 72° C., 10 minutes The PCR products were separated by 0.8% agarose gel electrophoresis, purified and cloned into pGEMT-Easy (Promega) by TA cloning method to generate pGEMT-Easy-GI, which was digested with NdeI and EcoRI and purified after separated by 0.8% agarose gel electrophoresis. The fragment was ligated with NdeI and EcoRI digested pRSET-lac-kan vector to generate pRSET-lac-GI-kan. 10 primer pair sequences (Table 3) were designed based on known hok/sok DNA sequences (GenBank X05813). The construction of PCR gene was performed according to Kikuchi, M. et al., 1999, Gene 236:159-167, with modifications in some steps. The PCR amplification condition was: 20 ng of each primer, 50 μM dATP, 50 μM dTTP, 50 μM dCTP, 50 μM dGTP, 20 mM Tris-HCl (pH 8.8), 10 mM KCl, 10 mM (NH₄)₂SO₄, 2 mM MgSO₄, 0.1% Triton X-100, 2.5 U Pfu DNA polymerase (Promega), and the volume was adjusted to 50 μL with sterile distilled water. PCR amplification was programmed as follows: 95° C., 4 minutes; then 30 cycles of 94° C., 1.5 minutes; 50° C., 1.5 minutes; 72° C., 5 minutes; and 72° C., 10 minutes. 5 μL PCR reaction mixture was amplified with primers 1 and 10 under the same condition. PCR product of 580 bp in length was obtained with 5' and 3' ends containing AscI and EcoRI restriction sites respectively. The PCR products were separated by 0.8% agarose gel electrophoresis, purified, and digested with AscI and EcoRI. The fragment was ligated with AscI and EcoRI digested pRSET-lac-GI-kan to generate pRSET-lac-GI-hok/sok-kan.

TABLE 3

| No. | Primer Sequence |
|---|---|
| 1 | 5'-ttggcgcgccttaagatatcaacaaactccgggaggcagc gtgatgcggcaacaatcacacggatttcccgtgaa-3' (SEQ ID NO: 31) |
| 2 | 5'-catatacctgcacgctgaccacactcactttccctgaaaa taatccgctcattcagaccgttcacgggaaatccgtgtga-3' (SEQ ID NO: 32) |
| 3 | 5'-ggtcagcgtgcaggtatatgggctatgatgtgcccggcgc ttgaggctttctgcctcatgacgtgaaggtggtttgttgc-3' (SEQ ID NO: 33) |
| 4 | 5'-cgtggtggttaatgaaaattaacttactacggggctatct tctttctgccacacaacacggcaacaaaccaccttcacgt-3' (SEQ ID NO: 34) |

TABLE 3-continued

| No. | Primer Sequence |
|---|---|
| 5 | 5'-aattttcattaaccaccacgaggcatccctatgtctagtc cacatcaggatagcctcttaccgcgctttgcgcaaggaga-3' (SEQ ID NO: 35) |
| 6 | 5'-tgagacacacgatcaacacacaccagacaagggaacttcg tggtagtttcatggccttcttctccttgcgcaaagcgcgg-3' (SEQ ID NO: 36) |
| 7 | 5'-tgtgttgatcgtgtgtctcacactgttgatattcacttat ctgacacgaaaatcgctgtgcgagattcgttacagagacg-3' (SEQ ID NO: 37) |
| 8 | 5'-cgcctccaggttgctacttaccggattcgtaagccatgaa agccgccacctccctgtgtccgtctctgtaacgaatctcg-3' (SEQ ID NO: 38) |
| 9 | 5'-taagtagcaacctggaggcgggcgcaggcccgcctttca ggactgatgctggtctgactactgaagcgcctttataaag-3' (SEQ ID NO: 39) |
| 10 | 5'-cggaattcacaacatcagcaaggagaaaggggctaccggc gaaccagcagcccctttataaaggcgcttcagt-3' (SEQ ID NO: 40) |

A DNA fragment of 1,074 bp in length (containing D-amino acid oxidase mutant GHA gene) was obtained after the plasmid pRSET-kan-DAOGHA (China Patent Application Publication No: CN1680558A) was digested with NdeI and BglII. The fragment was separated by 0.8% agarose gel electrophoresis, purified, and ligated with NdeI and BglII digested pRSET-lac-GI-hok/sok-kan to generate pHS-GHA (see SEQ 3 in the Sequence Listing). The competent cells of *E. coli* BL21(DE3) pLysS Novagen) were transformed with pHS-GHA to generate strain BL-HS-GHA.

The preparation of the cells of BL-HS-GHA (*E. coli* BL21 (DE3) pLysS containing recombinant D-amino acid oxidase GHA) was as follows:

Single colony of the cells of *E. coli* BL-HS-GHA was isolated from LB agar plate medium containing kanamycin (50 μg/mL) and inoculated into 2×5 ml LB broths containing kanamycin (50 μg/mL). The cells were incubated at 37° C. for 8 hours (the rotation rate of shaker was 250 rpm) and inoculated into 2×50 ml seed media containing kanamycin (100 μg/mL) and chloramphenicol (40 μg/mL). The cells were incubated at 30° C. for 16 hours (the rotation rate of shaker was 400 rpm).

Preparation of Corn Steep Liquid 1:

300 grams of corn steep solid (from North China Pharmaceutical Kangxin Co Ltd) were dissolved in 300 mL distilled water, mixed and centrifuged (5,000 g, 8 minutes). The supernatant was corn steep liquid 1. The precipitate was reserved for future use.

Preparation of Corn Steep Liquid 2:

The precipitate obtained was dissolved in 600 mL distilled water, mixed and centrifuged (5,000 g, 8 minutes). The supernatant was corn steep liquid 2.

50 mL seed medium containing the following components:

| Corn steep liquid 1 | 4 mL |
|---|---|
| Corn steep liquid 2 | 4 mL |
| Yeast extract | 0.2 g |
| Ammonium sulphate | 0.075 g |
| Disodium hydrogen phosphate | 0.25 g |
| Potassium dihydrogen phosphate | 0.04 g |
| Sodium chloride | 0.075 g |

The mixture was dissolved in 50 mL distilled water and the pH was adjusted to 7.15 with 10N sodium hydroxide, and then the solution was sterilized at high temperature.

The seed was fermented overnight and a total of 100 mL of seed was inoculated to a 2 L fermentation tank (BIOENGINEERING, Benchtop Fermentor, KLF2000) containing kanamycin (50 μg/mL).

The components of a 2 L fermentation medium were shown as follows:

| Corn steep liquid 1 | 160 mL |
|---|---|
| Corn steep liquid 2 | 160 mL |
| Yeast extract | 8 g |
| Ammonium sulphate | 3 g |
| Disodium hydrogen phosphate | 10 g |
| Potassium dihydrogen phosphate | 1 g |
| Sodium chloride | 3 g |

The mixture was dissolved in 1.9 L distilled water and the pH was adjusted to 7.15 with 10N sodium hydroxide, and then the solution was sterilized at high temperature in the 2 L fermentation tank (BIOENGINEERING, Benchtop Fermentor, KLF2000).

Glucose (12.5 g) was dissolved in 50 mL distilled water and the solution was sterilized at high temperature. Magnesium sulfate (1.25 g) was dissolved in 50 mL distilled water and the solution was sterilized at high temperature. The sterilized glucose and magnesium sulfate were placed in the 2 L fermentation tank before fermentation.

Preparation of the Supplements

Corn steep liquid 1 and corn steep liquid 2 of 250 mL respectively were mixed and the pH of the mixture was adjusted to 7.25 with 10N sodium hydroxide, and then the mixture was sterilized at high temperature.

60 mL distilled water containing 2.25 g ammonium sulfate, 7.56 g disodium hydrogen phosphate, 1.2 g potassium dihydrogen phosphate and 2.25 g sodium chloride was sterilized at high temperature.

15 grams of yeast extract were dissolved in 100 mL distilled water, and then the solution was sterilized at high temperature.

70 grams of glucose were dissolved in 140 mL distilled water, and then the solution was sterilized at high temperature.

30 mL of glycerol was mixed with 10 mL distilled water, and then the solution was sterilized at high temperature.

20 grams of magnesium sulfate were dissolved in 30 mL distilled water, and then the solution was sterilized at high temperature.

The above solutions were mixed and kanamycin was added to a final concentration of 50 μg/mL. 2 mL anti-foam agent was added.

The cells were grown at 35° C. The supplements were added (50 mL/hour) when the pH of the solution increased from 6.9 to 7.2 in the first 6 hours. The cells were allowed to grow for another 26 hours under the equilibrium condition (pH was maintained at 7.2 bp 5 N sodium hydroxide and the dissolved oxygen content pO$_2$ was less than 0.5%).

After the fermentation, the mixture was centrifuged at 4° C. (5,000 g, 8 minutes) to remove the supernatant and get a cell pellet of 198 g. The cells was resuspended in 600 mL of sodium phosphate buffer (50 mM, pH7.5) and was disrupted in a dyno-mill (DYNO-MILL TYP KL, 0.2 mm diameter beads, WA Bachofen) at a flow rate of 50 mL/minute. The residual cells were washed out with 800 mL of sodium phosphate buffer (50 mM, pH 7.5). The lysed cells suspension was incubated in water bath at 55° C. for 30 minutes, centrifuged at high speed (10,000, 30 minutes) to get the supernatant, which contained crude recombinant D-amino acid oxidase GHA. The purification of the D-amino acid oxidase was performed according to Alonso, J., Barredo, J. L., Diez, B., Mellado, E., Salto, F., Garcia, J. L., Cortes, E. (1998, Microbiology 144:1095-1101). Glycerol was added to the crude D-amino acid oxidase GHA to a final concentration of 10%, and the pH was adjusted to 8 by 5N sodium hydroxide, and then the mixture was centrifuged (13,000 g, 30 minutes) to collect the supernatant. DEAE-cellulose ion exchange resins (Sigma, D-0909) were prepared according to manufacturer's instruction. Each 1 mL of crude enzyme extract was mixed with 0.5 mL DEAF-cellulose ion exchange resins and the mixture was stirred at 4° C. for 5 hours (100 rpm/minute). The enzyme solution was filtered by a filtration funnel (Buchner filter funnel, 120 mm P1). DEAE-cellulose ion exchange resins were washed with 3 volumes of 40 mM potassium dihydrogen phosphate buffer (containing 10% glycerol), then 2 volumes of 400 mM potassium dihydrogen phosphate buffer to elute the recombinant D-amino acid oxidase GHA. Ammonium sulfate weighted 262 g was added to each 1 L eluted D-amino acid oxidase GHA and the mixture was stirred at room temperature for 15 minutes (100 rpm/minute) and centrifuged (13,000 g, 15 minutes) to remove the supernatant and collect the pellet. The precipitate was dissolved in 20 mM potassium dihydrogen phosphate buffer (pH7.5) and ultrafiltrated with Millipore YM30 membrane to remove residual ammonium sulfate, therefore the enzyme solution was concentrated to 25 mg/mL. The purity of the protein was determined by SDS-PAGE. Bovine serum (ovalbumin) weighted 3.75 g and 112.5 ml water were added to 25 ml of D-amino acid oxidase enzyme solution (25 mg/mL) and the mixture was stirred thoroughly to generate diluted enzyme solution.

5 grams of melamine foam was cut into cubes of 15 mm$^3$ and placed in a nylon mesh bag. Then immobilization was performed as follows: a) 50 ml of diluted enzyme solution was added to the foam cubes, which were pressed by hand to make the components mixed to uniformity; b) 400 ml of 0.05% PEI solution (pH 7.0) was added into the foams, which were pressed by hand for at least 5 minutes to make the components mixed, and then pressed by hand again to remove unadsorbed liquid; c) 400 ml of 0.05% glutaraldehyde solution was added into the foams, which were pressed by hand repeatedly to make the component mixed, kept to stand for 5 minutes, and then pressed by hand again to remove unadsorbed liquid; d) the steps (a) to (c) were repeated three times, then the foams were pressed by hand and washed with water three times, and pressed by hand again to remove unadsorbed liquid, after that the foams were dried under flow air for 5-10 hours. 30 grams granules of immobilized *E. coli* cells containing expressed D-amino acid oxidase were obtained.

The activity of the enzyme was measured according to Isogai, T., Ono, H., Ishitani, Y., Kojo, H., Ueda, Y., Kohsaka, M. (1990, J Biochem [Tokyo]. 108, 1063-1069), with modifications in some steps. Specifically, 5 g of the immobilized *E. coli* containing expressed D-amino acid oxidase was resuspended in 75 mM cephalosporin C aqueous sodium supplemented with oxygen. The mixture was reacted at 22° C. for 60 minutes with shaking. 100 μl of reaction mixture was collected at time of 0, 15, 30 minutes and mixed with 10 μl of 3% hydrogen peroxide. The reaction was terminated by mixing with 50 μl of 10% TCA and the mixture was centrifuged (10,000 g, 3 minutes). 10 μl supernatant was mixed with 990 μl HPLC mobile phase, and the mixture was loaded onto HPLC column for detection. HPLC column: Diamonsil™ C18, 250 4.6 mm (Dikma Technologies, Beijing); mobile phase: 50 mM $K_2HPO_4/K_2PO_4$ (pH 7.0), 5% acetonitrile; column temperature: 30° C.; flow rate: 1 ml/minute; detection wavelength: 260 nm UV. 1 unit of enzyme activity is defined as the amount of enzyme required to convert 1 μmole of cephalosporin C into glutaryl-7-aminocephalosporanic acid in 1 minute under the above condition. The specific activity of the immobilized enzymes prepared in Example 8 was 156 U/g in the initial 15 minutes.

Example 9

Immobilization of *E. coli* Cells Containing Expressed Glucose Isomerase on Strip Carriers The cells were prepared as described in Example 2 and suspended in 5 volumes of distilled water. The melamine foam (4.8 g) was cut into strips of dimension of 0.5×10×120 cm. Then immobilization was performed as follows: a) the foam strips were immersed in cell suspension, and pressed by hand to ensure even distribution of cell suspension inside the foam, squeezed by going through a pair of rollers to remove unadsorbed solution. The gap between the two rollers was adjusted so that 200 g of the cell suspension was adsorbed on the foam; b) 500 ml of 0.1% PEI (pH 7.0) was added into the foam; pressed by hand to ensure the even distribution of PEI the unadsorbed solution was removed by make the foam go through the rollers again; c) 500 ml of 0.1% glutaraldehyde solution was added into the foam, pressed by hand to ensure even distribution of the liquid and removal of unadsorbed liquid, and then the foam was allowed to stand for 5 minutes; d) steps (a) to (c) were repeated five times. The gap between the rollers was adjusted in step (a) so that about 100 g of cell suspension was adsorbed. The foam was washed and pressed by hand in water once, and then squeezed to remove unadsorbed liquid. 24 grams of immobilized *E. coli* cell strips containing glucose isomerase were obtained after the foam was dried under flow air for 5-10 hours. The enzyme activity was measured as described in Example 2 using a small portion of the cell strip. The enzyme specific activity was 6,608 U/g.

Example 10

Reel-Like Cylindrical Column with Immobilized *E. coli* Cells Containing Expressed Glucose Isomerase A portion (3.5 g) of the strips having cells immobilized thereon prepared in Example 9 was wound along a cylindrical core (FIG. 1, *a*) to form a column of 1.8 cm in diameter, 9.6 cm in height (FIG. 1, *b*). Before the winding, both ends of the foam strips were cut to slanted surfaces to prevent the development of gap between the inner core and the outer wall. The column surface was wrapped with rubber band of 4 cm width (FIG. 1, *c*). The two interface devices (FIG. 1, *d*) were fixed on both ends of the column by rubber band, sealed with glass glue and connected to silicone tube (FIG. 1, *e*). The column was wrapped using polyurethane insulation material (FIG. 1, *f*).

50% (w/v) glucose syrup (containing 2.5 mM phosphate, 0.5 mM $MgCl_2$, 0.05 mM $CoCl_2$, pH 6.5) of 75° C. was passed through the column at an initial flow rate of 1.62 ml/minute; the effluent contained 51.6% by weight of fructose of total sugar amount. After 144 hours, the flow rate was 1.63 ml/minute and the effluent contained 45.6% fructose of the total sugar amount.

The reel-like cylindrical column prepared in this invention is simpler and more efficient than granules of immobilized enzymes in terms of installation and removal, which is an advantage in large scale production. It also reduces the fixed investment. In addition, to meet variation in production scale, the column can be used alone or in combination of variable number in parallel or in series and in length. Also, the enzyme activity reduces gradually during the process of operation: the closer to the entry end, the faster it loses the activity. After a period of time, there is significant variation of the enzyme activity between the entry and outlet ends. Using the products of this invention, those columns of diminished activity can be easily replaced by the new columns of the immobilized enzymes/cells and thus the life and productivity of the entire device is improved. This cannot be done by the existing granules of immobilized enzyme.

Example 11

Immobilization of Glucose Isomerase on Lattice Structure-Like Strips

The bacterial cells prepared in Example 2 were resuspended in 3 volumes of distilled water and disrupted by the high pressure homogenizer (Niro Soavi S.P.A., Type NS1001L 2K). The obtain liquid was heat-treated at 80° C. for 5 minutes and centrifuged, and then the supernatant was concentrated to 15 mg/ml protein concentration by passing through ultra-filtration membrane of 10,000 molecular weight cutoff to obtain crude glucose isomerase enzyme solution. Aldehyde glucose isomerase solution was generated by adding 65 ml 1% glutaraldehyde solution into 650 ml of the crude enzyme solution, and mixing the mixture for 30 minutes with gentle stirring.

Melamine foam was cut into strips of dimension of 0.5× 50×125 cm (3.25 g) and immobilization was performed as follows: a) 130 ml of aldehyde glucose isomerase solution prepared as above was added into foam strips, which were pressed by hand to distribute the solution evenly inside the foam; b) 130 ml of 0.25% PEI was added to the foam strips, which were pressed by hand repeatedly to make the components mixed to distribute the enzyme and PEI solution evenly and react fully, the foam strips were pressed by hand until the liquid was completely clear, and then the foam strips were pressed by hand again to remove the liquid in the foam; c) the steps (a) to (b) were repeated four times, and the foam strips were pressed by hand and washed with water twice, then the foam strips were pressed by hand again to remove unadsorped liquid, and dried under flow air for 5-10 hours to obtain 21.6 g of lattice-like strips having glucose isomerase immobilized thereon. The specific activity of the immobilized enzymes was 6,330 U/g. The glucose isomerase activity was measured as described in Example 2.

The disclosure of the cited literatures and patent applications were incorporated herein by reference. This invention is not limited by the detailed description in the Examples above. Various modifications can be made by those skilled in the field and these modifications should be regarded as within the scope of the claims of the invention.

What is claimed is:

1. A method for preparing immobilized enzymes, comprising the following steps:
   a) preparing melamine foam as an immobilization carrier; and
   b) flocculation and crosslinking the enzymes on the carrier wherein the carrier has a water natural wetting rate of at least 0.2 mm/s, and wherein the water natural wetting rate is the ratio of the vertical height of the wetted portion, including the portion immersed in water, of the organic porous material to the time taken.

2. The method according to claim 1, wherein the shape of the carrier is selected from the group consisting of granules, straps, sheets, columns, and blocks.

3. The method according to claim 2, wherein the carrier is a strap shape material capable of being wound into a reel-like cylindrical column, and wherein the reel-like cylindrical column may be employed as a reaction column.

4. The method according to claim 1, wherein the flocculation and crosslinking are accomplished by using a protein flocculation agent and a multi-aldehyde compound, and wherein the enzyme proteins or cells are flocculated, crosslinked with and deposited onto the pore walls of the carrier.

5. The method according to claim 4, wherein the protein flocculation agent is selected from the group consisting of chitosan, polyethyleneimine (PEI), and carboxymethyl polyethyleneimine.

6. The method according to claim 4, wherein the multi-aldehyde compound is glutaraldehyde, dialdehyde starch, glucan di-aldehyde.

7. The method according to claim 1, wherein the immobilized enzyme is selected from the group consisting of glucose isomerase, D-amino acid oxidase, glutaryl-7-aminocephalosporanic acid acylase, and adenosylmethionine synthetase.

8. The method according to claim 1, wherein the immobilized enzyme is expressed in cells.

9. The method according to claim 8, wherein the cells are *E. coli* cells.

10. The method according to claim 1, wherein the flocculation and crosslinking the enzymes on the carrier repeats several times.

* * * * *

UNITED STATES PATENT AND TRADEMARK OFFICE
CERTIFICATE OF CORRECTION

PATENT NO. : 8,486,676 B2  Page 1 of 1
APPLICATION NO. : 12/097671
DATED : July 16, 2013
INVENTOR(S) : Jin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1320 days.

Signed and Sealed this
Eighth Day of September, 2015

Michelle K. Lee
*Director of the United States Patent and Trademark Office*

SEQUENCE LISTING

<160> NUMBER OF SEQ ID NOS: 40

<210> SEQ ID NO 1
<211> LENGTH: 1320
<212> TYPE: DNA
<213> ORGANISM: Thermoanaerobacterium saccharolyticum

<400> SEQUENCE: 1

```
atgaataaat attttgagaa cgtatctaaa ataaaatatg aaggaccaaa atcaaataat      60
ccttattcct ttaaatttta caatccagag gaagtaatcg atggcaagac gatggaggag     120
catctccgct tttctatagc ttattggcac acttttactg ctgatggaac agatcaattt     180
ggcaaggcta ctatgcaaag accatggaac cactacacag atcctatgga tatagcgaaa     240
gcaagggtag aagcagcatt tgagttttt gataagataa atgcacfttt cttctgcttc      300 catgataggg atattgcccc tgaaggagat actcttagag agacaaacaa aaacttagat     360
acaatagttg ctatgataaa ggattactta aagaccagca agacaaaagt tttgtggggt     420
accgcaaatc ttttctccaa tccgagattt gtacatggtg catcaacatc ctgcaatgct     480
gacgtttttg catattctgc agcgcaagtc aaaaaagccc ttgagattac taaggagctt     540
ggccgcgaaa actacgtatt ttggggtgga agagaagggt acgagacgct tctcaataca     600
gatatggagt tagagcttga taactttgca agatttttgc acatggctgt tgactatgca     660
aaggaaatcg gctttgaagg tcagttcttg attgagccga agccaaagga gcctacaaaa     720
catcaatacg actttgacgt ggcaaatgta ttggcattct tgagaaaata cgaccttgac     780
aaatatttca aagtaaatat cgaagcaaac catgcgacat ggcattcca cgacttccaa     840 catgagctaa gatacgccag aataaacggt gtattaggat caattgacgc aaatacaggc     900
```

-continued

```
gacatgcttt tgggatggga tacggaccag ttccctacag atatacgcat gacaacgctt      960
gctatgtatg aagtcataaa gatgggtgga tttgacaaag gtggccttaa ctttgatgca     1020
aaagtaagac gtgcttcatt tgagccagaa gatcttttct taggtcacat agcaggaatg     1080
gatgcttttg caaaaggctt taaagttgct tacaagcttg tgaaagatgg cgtatttgac     1140
aagttcatcg aagaaagata cgcaagctac aaagaaggca ttggcgctga tattgtaagc     1200
ggtaaagctg acttcaagag ccttgaaaag tatgcattag agcacagcca gattgtaaac     1260
aaatcaggca gacaagagct attagaatca atcctaaatc agtatttgtt tgcagaataa     1320
```

<210> SEQ ID NO 2
<211> LENGTH: 439
<212> TYPE: PRT
<213> ORGANISM: Thermoanaerobacterium saccharolyticum

<400> SEQUENCE: 2

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
```

```
            305                 310                 315                 320
Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 3
<211> LENGTH: 1320
<212> TYPE: DNA
<213> ORGANISM: Thermoanaerobacterium saccharolyticum
<220> FEATURE:
<221> NAME/KEY: misc_feature
<222> LOCATION: (259)..(261)
<223> OTHER INFORMATION: "n" represents a,t,g or c; and "nnn" represents
      any amino acid code except for phenylalanine.
<220> FEATURE:
<221> NAME/KEY: misc_feature
<222> LOCATION: (649)..(651)
<223> OTHER INFORMATION: "n" represents a,t,g or c; and "nnn" represents
      any amino acid code except for Valine.
<220> FEATURE:
<221> NAME/KEY: misc_feature
<222> LOCATION: (778)..(780)
<223> OTHER INFORMATION: "n" represents a,t,g or c; and "nnn" represents
      any amino acid code except for aspartic acid.
<220> FEATURE:
<221> NAME/KEY: misc_feature
<222> LOCATION: (826)..(828)
<223> OTHER INFORMATION: "n" represents a,t,g or c; and "nnn" represents
      any amino acid code except for phenylalanine.

<400> SEQUENCE: 3
atgaataaat attttgagaa cgtatctaaa ataaatatg aaggaccaaa atcaataat      60 ccttattcct ttaaatttta caatccagag gaagtaatcg atggcaagac gatggaggag   120
catctccgct tttctatagc ttattggcac acttttactg ctgatggaac agatcaattt   180
ggcaaggcta ctatgcaaag accatggaac cactacacag atcctatgga tatagcgaaa   240
gcaagggtag aagcagcann ngagttttt gataagataa atgcaccttt cttctgcttc    300
catgataggg atattgcccc tgaaggagat actcttagag agacaaacaa aaacttagat   360
acaatagttg ctatgataaa ggattactta agaccagca agacaaaagt tttgtggggt    420
accgcaaatc ttttctccaa tccgagattt gtacatggtg catcaacatc ctgcaatgct   480 gacgttttttg catattctgc agcgcaagtc aaaaaagccc ttgagattac taaggagctt    540
ggccgcgaaa actacgtatt tgggggtgga agagaagggt acgagacgct tctcaataca   600
gatatggagt tagagcttga taactttgca agatttttgc acatggctnn ngactatgca   660
aaggaaatcg gctttgaagg tcagttcttg attgagccga agccaaagga gcctacaaaa   720
catcaatacg actttgacgt ggcaaatgta ttggcattct tgagaaaata cgaccttnnn   780
```

```
aaatatttca aagtaaatat cgaagcaaac catgcgacat tggcannnca cgacttccaa    840
catgagctaa gatacgccag aataaacggt gtattaggat caattgacgc aaatacaggc    900
gacatgcttt tgggatggga tacggaccag ttccctacag atatacgcat gacaacgctt    960
gctatgtatg aagtcataaa gatgggtgga tttgacaaag gtggccttaa ctttgatgca   1020
aaagtaagac gtgcttcatt tgagccagaa gatctttcct taggtcacat agcaggaatg   1080 gatgctttg caaaaggctt taaagttgct tacaagcttg tgaaagatgg cgtatttgac    1140
aagttcatcg aagaaagata cgcaagctac aaagaaggca ttggcgctga tattgtaagc   1200
ggtaaagctg acttcaagag ccttgaaaag tatgcattag agcacagcca gattgtaaac   1260
aaatcaggca gacaagagct attagaatca atcctaaatc agtatttgtt tgcagaataa   1320
```

<210> SEQ ID NO 4
<211> LENGTH: 439
<212> TYPE: PRT
<213> ORGANISM: Thermoanaerobacterium saccharolyticum
<220> FEATURE:
<221> NAME/KEY: MISC_FEATURE
<222> LOCATION: (87)..(87)
<223> OTHER INFORMATION: Xaa represents any amino acid residue other
      than phenylalanine.
<220> FEATURE:
<221> NAME/KEY: MISC_FEATURE
<222> LOCATION: (217)..(217)
<223> OTHER INFORMATION: Xaa represents any amino acid residue other
      than Valine.
<220> FEATURE:
<221> NAME/KEY: MISC_FEATURE
<222> LOCATION: (260)..(260)
<223> OTHER INFORMATION: Xaa represents any amino acid residue other
      than aspartic acid.
<220> FEATURE:
<221> NAME/KEY: MISC_FEATURE
<222> LOCATION: (276)..(276)
<223> OTHER INFORMATION: Xaa represents any amino acid residue other
      than phenylalanine.

<400> SEQUENCE: 4

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Xaa Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
```

```
                    180                 185                 190
Gly Tyr Glu Thr Leu Leu Asn Thr Asp Met Glu Leu Glu Leu Asp Asn
            195                 200                 205

Phe Ala Arg Phe Leu His Met Ala Xaa Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Xaa Lys Tyr Phe Lys Val Asn Ile Glu Ala Asn His Ala
            260                 265                 270

Thr Leu Ala Xaa His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Ser Ile Leu
            420                 425                 430

Asn Gln Tyr Leu Phe Ala Glu
            435

<210> SEQ ID NO 5
<211> LENGTH: 439
<212> TYPE: PRT
<213> ORGANISM: Thermoanaerobacterium saccharolyticum

<400> SEQUENCE: 5

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
```

```
            115                 120                 125
Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 6
<211> LENGTH: 439
<212> TYPE: PRT
<213> ORGANISM: Thermoanaerobacterium saccharolyticum

<400> SEQUENCE: 6

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
```

```
            50              55              60
Met Gln Arg Pro Trp Asn His Tyr Thr Asp Pro Met Asp Ile Ala Lys
 65                  70                  75                  80

Ala Arg Val Glu Ala Ala Met Glu Phe Phe Asp Lys Ile Asn Ala Pro
                 85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
            130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435
```

<210> SEQ ID NO 7
<211> LENGTH: 439
<212> TYPE: PRT
<213> ORGANISM: Thermoanaerobacterium saccharolyticum

<400> SEQUENCE: 7

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Arg Asp Tyr Ala Lys Glu Ile Gly
210                 215                 220

Phe Glu Gly Gln Phe Leu Ile Glu Pro Lys Pro Lys Gly Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415
```

-continued

```
Gln Ile Val Asn Lys Ser Gly Arg Gln Glu Leu Leu Glu Ser Ile Leu
                420                 425                 430
Asn Gln Tyr Leu Phe Ala Glu
            435

<210> SEQ ID NO 8
<211> LENGTH: 439
<212> TYPE: PRT
<213> ORGANISM: Thermoanaerobacterium saccharolyticum

<400> SEQUENCE: 8

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Trp Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350
```

```
Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
                435

<210> SEQ ID NO 9
<211> LENGTH: 439
<212> TYPE: PRT
<213> ORGANISM: Thermoanaerobacterium saccharolyticum

<400> SEQUENCE: 9

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu His Leu Arg Phe Ser Ile Ala Tyr
                35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
        180                 185                 190

Gly Tyr Glu Thr Leu Leu Asn Thr Asp Met Glu Leu Glu Leu Asp Asn
    195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Glu Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
    275                 280                 285
```

```
Asn Gly Val Leu Gly Ser Ile Asp Ala Asn Gln Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 10
<211> LENGTH: 439
<212> TYPE: PRT
<213> ORGANISM: Thermoanaerobacterium saccharolyticum

<400> SEQUENCE: 10

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220
```

```
Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Gly His Asp Phe Gln His Glu Leu Arg Tyr Ala Arg Ile
    275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Ser Ile Leu
            420                 425                 430

Asn Gln Tyr Leu Phe Ala Glu
            435

<210> SEQ ID NO 11
<211> LENGTH: 439
<212> TYPE: PRT
<213> ORGANISM: Thermoanaerobacterium saccharolyticum

<400> SEQUENCE: 11

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160
```

```
Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Ala Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Ser Ile Leu
            420                 425                 430

Asn Gln Tyr Leu Phe Ala Glu
        435

<210> SEQ ID NO 12
<211> LENGTH: 439
<212> TYPE: PRT
<213> ORGANISM: Thermoanaerobacterium saccharolyticum

<400> SEQUENCE: 12

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95
```

Phe Phe Cys Phe His Asp Arg Asp Ile Ala Pro Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Thr His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 13
<211> LENGTH: 439
<212> TYPE: PRT
<213> ORGANISM: Thermoanaerobacterium saccharolyticum

<400> SEQUENCE: 13

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
             35                  40                  45

Trp His Thr Phe Thr Ala Asp Gly Thr Asp Gln Phe Gly Lys Ala Thr
     50                  55                  60

Met Gln Arg Pro Trp Asn His Tyr Thr Asp Pro Met Asp Ile Ala Lys
 65                  70                  75                  80

Ala Arg Val Glu Ala Ala Leu Glu Phe Phe Asp Lys Ile Asn Ala Pro
                 85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Gly Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Thr His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 14

```
<211> LENGTH: 439
<212> TYPE: PRT
<213> ORGANISM: Thermoanaerobacterium saccharolyticum

<400> SEQUENCE: 14

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Gly Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Ala Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400
```

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 15
<211> LENGTH: 31
<212> TYPE: DNA
<213> ORGANISM: Artificial Sequence
<220> FEATURE:
<223> OTHER INFORMATION: RBS Forward primer

<400> SEQUENCE: 15
catatgtata tctccttctt gtgtgaaatt g                            31

<210> SEQ ID NO 16
<211> LENGTH: 28
<212> TYPE: DNA
<213> ORGANISM: Artificial Sequence
<220> FEATURE:
<223> OTHER INFORMATION: RBS Reverse primer

<400> SEQUENCE: 16
cagtggctgc tgccagtggc gataagtc                               28

<210> SEQ ID NO 17
<211> LENGTH: 56
<212> TYPE: DNA
<213> ORGANISM: Artificial Sequence
<220> FEATURE:
<223> OTHER INFORMATION: T1 Primer

<400> SEQUENCE: 17
agcctaggtt aattaacttt aagaaggaga tatacatatg aataaatatt ttgaga    56

<210> SEQ ID NO 18
<211> LENGTH: 33
<212> TYPE: DNA
<213> ORGANISM: Artificial Sequence
<220> FEATURE:
<223> OTHER INFORMATION: 85LR primer

<400> SEQUENCE: 18
aaaaactcca gtgctgcttc taccttgct ttc                          33

<210> SEQ ID NO 19
<211> LENGTH: 31
<212> TYPE: DNA
<213> ORGANISM: Artificial Sequence
<220> FEATURE:
<223> OTHER INFORMATION: 87LF primer

<400> SEQUENCE: 19
gaagcagcac tggagttttt tgataagata a                           31

<210> SEQ ID NO 20
<211> LENGTH: 30
<212> TYPE: DNA
<213> ORGANISM: Artificial Sequence
<220> FEATURE:
<223> OTHER INFORMATION: 217GR Primer

<400> SEQUENCE: 20
gcatagtcgc cagccatgtg caaaaatctt                                              30

<210> SEQ ID NO 21
<211> LENGTH: 30
<212> TYPE: DNA
<213> ORGANISM: Artificial Sequence
<220> FEATURE:
<223> OTHER INFORMATION: 217GF primer

<400> SEQUENCE: 21
acatggctgg cgactatgca aaggaaatcg                                              30

<210> SEQ ID NO 22
<211> LENGTH: 30
<212> TYPE: DNA
<213> ORGANISM: Artificial Sequence
<220> FEATURE:
<223> OTHER INFORMATION: 260AR primer

<400> SEQUENCE: 22
aaatatttcg caaggtcgta ttttctcaag                                              30

<210> SEQ ID NO 23
<211> LENGTH: 30
<212> TYPE: DNA
<213> ORGANISM: Artificial Sequence
<220> FEATURE:
<223> OTHER INFORMATION: 260AF primer

<400> SEQUENCE: 23
acgaccttgc gaaatatttc aaagtaaata                                              30

<210> SEQ ID NO 24
<211> LENGTH: 38
<212> TYPE: DNA
<213> ORGANISM: Artificial Sequence
<220> FEATURE:
<223> OTHER INFORMATION: T2 primer

<400> SEQUENCE: 24
ataagctcag cggcgcgcct tattctgcaa acaaatac                                     38

<210> SEQ ID NO 25
<211> LENGTH: 26
<212> TYPE: DNA
<213> ORGANISM: Artificial Sequence
<220> FEATURE:
<223> OTHER INFORMATION: ACY-Forward primer

<400> SEQUENCE: 25
catatgaacg ctcccgtccc cgtccc                                                  26

<210> SEQ ID NO 26
<211> LENGTH: 26
<212> TYPE: DNA
<213> ORGANISM: Artificial Sequence
<220> FEATURE:
<223> OTHER INFORMATION: ACY-Reverse primer

<400> SEQUENCE: 26
agatcttcag atggtgaagc gggcac                                                  26

<210> SEQ ID NO 27
<211> LENGTH: 56
<212> TYPE: DNA
<213> ORGANISM: Artificial Sequence
<220> FEATURE:

```
<223> OTHER INFORMATION: SAM-Forward primer

<400> SEQUENCE: 27
agcctaggtt aattaacttt aagaaggaga tatacatatg agaaacataa ttgtaa        56

<210> SEQ ID NO 28
<211> LENGTH: 44
<212> TYPE: DNA
<213> ORGANISM: Artificial Sequence
<220> FEATURE:
<223> OTHER INFORMATION: SAM-R

<400> SEQUENCE: 28
ataagctcag cggcgcgcct tagaatgtag ttactttttcc ttca                    44

<210> SEQ ID NO 29
<211> LENGTH: 56
<212> TYPE: DNA
<213> ORGANISM: Artificial Sequence
<220> FEATURE:
<223> OTHER INFORMATION: Thermoanaerobacterium saccharolyticum glucose
      isomerase Forward Primer

<400> SEQUENCE: 29
agcctaggtt aattaacttt aagaaggaga tatacatatg aataaatatt ttgaga        56

<210> SEQ ID NO 30
<211> LENGTH: 38
<212> TYPE: DNA
<213> ORGANISM: Artificial Sequence
<220> FEATURE:
<223> OTHER INFORMATION: Thermoanaerobacterium saccharolyticum glucose
      isomerase Reverse primer

<400> SEQUENCE: 30
ataagctcag cggcgcgcct tattctgcaa acaaatac                            38

<210> SEQ ID NO 31
<211> LENGTH: 75
<212> TYPE: DNA
<213> ORGANISM: Artificial Sequence
<220> FEATURE:
<223> OTHER INFORMATION: hok/sok primer 1

<400> SEQUENCE: 31
ttggcgcgcc ttaagatatc aacaaactcc gggaggcagc gtgatgcggc aacaatcaca    60
cggatttccc gtgaa                                                    75

<210> SEQ ID NO 32
<211> LENGTH: 80
<212> TYPE: DNA
<213> ORGANISM: Artificial Sequence
<220> FEATURE:
<223> OTHER INFORMATION: Hok/sok primer 2

<400> SEQUENCE: 32
catatacctg cacgctgacc acactcactt tccctgaaaa taatccgctc attcagaccg    60
ttcacgggaa atccgtgtga                                               80

<210> SEQ ID NO 33
<211> LENGTH: 80
<212> TYPE: DNA
<213> ORGANISM: Artificial Sequence
<220> FEATURE:
<223> OTHER INFORMATION: Hok/sok Primer 3
```

-continued

```
<400> SEQUENCE: 33
ggtcagcgtg caggtatatg ggctatgatg tgcccggcgc ttgaggcttt ctgcctcatg    60
acgtgaaggt ggtttgttgc                                                80

<210> SEQ ID NO 34
<211> LENGTH: 80
<212> TYPE: DNA
<213> ORGANISM: Artificial Sequence
<220> FEATURE:
<223> OTHER INFORMATION: Hok/sok Primer 4

<400> SEQUENCE: 34
cgtggtggtt aatgaaaatt aacttactac ggggctatct tctttctgcc acacaacacg    60
gcaacaaacc accttcacgt                                                80

<210> SEQ ID NO 35
<211> LENGTH: 80
<212> TYPE: DNA
<213> ORGANISM: Artificial Sequence
<220> FEATURE:
<223> OTHER INFORMATION: Hok/sok primer 5

<400> SEQUENCE: 35
aattttcatt aaccaccacg aggcatccct atgtctagtc cacatcagga tagcctctta    60
ccgcgctttg cgcaaggaga                                                80

<210> SEQ ID NO 36
<211> LENGTH: 80
<212> TYPE: DNA
<213> ORGANISM: Artificial Sequence
<220> FEATURE:
<223> OTHER INFORMATION: Hok/sok Primer 6

<400> SEQUENCE: 36
tgagacacac gatcaacaca caccagacaa gggaacttcg tggtagtttc atggccttct    60
tctccttgcg caaagcgcgg                                                80

<210> SEQ ID NO 37
<211> LENGTH: 80
<212> TYPE: DNA
<213> ORGANISM: Artificial Sequence
<220> FEATURE:
<223> OTHER INFORMATION: Hok/sok Primer 7

<400> SEQUENCE: 37
tgtgttgatc gtgtgtctca cactgttgat attcacttat ctgacacgaa aatcgctgtg    60
cgagattcgt tacagagacg                                                80

<210> SEQ ID NO 38
<211> LENGTH: 80
<212> TYPE: DNA
<213> ORGANISM: Artificial Sequence
<220> FEATURE:
<223> OTHER INFORMATION: Hok/sok Primer 8

<400> SEQUENCE: 38
cgcctccagg ttgctactta ccggattcgt aagccatgaa agccgccacc tccctgtgtc    60
cgtctctgta acgaatctcg                                                80

<210> SEQ ID NO 39
<211> LENGTH: 80
<212> TYPE: DNA
```

```
<213> ORGANISM: Artificial Sequence
<220> FEATURE:
<223> OTHER INFORMATION: Hok/sok sequence 9

<400> SEQUENCE: 39
taagtagcaa cctggaggcg ggcgcaggcc cgccttttca ggactgatgc tggtctgact    60
actgaagcgc ctttataaag                                                80

<210> SEQ ID NO 40
<211> LENGTH: 73
<212> TYPE: DNA
<213> ORGANISM: Artificial Sequence
<220> FEATURE:
<223> OTHER INFORMATION: Hok/sok Primer 10

<400> SEQUENCE: 40
cggaattcac aacatcagca aggagaaagg ggctaccggc gaaccagcag ccccttata    60 aaggcgcttc agt                                                       73
```